United States Patent
Dam

(10) Patent No.: US 8,694,271 B2
(45) Date of Patent: *Apr. 8, 2014

(54) APPARATUS AND METHOD FOR NON INVASIVE MEASUREMENT OF PROPERTIES OF A FLUID FLOWING IN A FLEXIBLE TUBING OR CONDUIT

(75) Inventor: Naim Dam, Muttontown, NY (US)

(73) Assignee: Hema-Q, Inc., Muttontown, NY (US)

( * ) Notice: Subject to any disclaimer, the term of this patent is extended or adjusted under 35 U.S.C. 154(b) by 581 days.

This patent is subject to a terminal disclaimer.

(21) Appl. No.: 12/959,496

(22) Filed: Dec. 3, 2010

(65) Prior Publication Data

US 2012/0143529 A1   Jun. 7, 2012

(51) Int. Cl.
*G01F 1/66* (2006.01)

(52) U.S. Cl.
USPC ................. 702/48; 702/108; 73/597; 73/598; 73/602; 73/617

(58) Field of Classification Search
USPC ........ 702/48, 108; 73/1.82, 597, 861.27, 598, 73/602, 612
See application file for complete search history.

(56) References Cited

U.S. PATENT DOCUMENTS

| | | | |
|---|---|---|---|
| 5,179,862 A | 1/1993 | Lynnworth |
| 5,453,576 A | 9/1995 | Krivitski |
| 5,663,503 A | 9/1997 | Dam et al. |
| 5,685,989 A | 11/1997 | Krivitski |
| 5,830,365 A | 11/1998 | Schneditz |
| 6,029,507 A | 2/2000 | Faber |
| 6,122,968 A | 9/2000 | Vandervalk |
| 6,165,151 A | 12/2000 | Weiner |
| 6,550,345 B1 | 4/2003 | Letton |
| 7,481,114 B2 | 1/2009 | Lynnworth |
| 7,838,296 B2 | 11/2010 | Corey |
| 2006/0052963 A1 | 3/2006 | Shkarlet |

*Primary Examiner* — Jonathan C Teixeira Moffat
*Assistant Examiner* — Hien Vo
(74) *Attorney, Agent, or Firm* — Leason Ellis LLP.

(57) ABSTRACT

Apparatus and method for non-invasive measuring of the sound velocity of a fluid, such as a liquid, flowing in a tubing having points of two different and known transverse length has one sensor mounted at each point connected to a circuit that provides signals to each sensor that are returned to it after passing through the tubing wall and flowing fluid and reflection from the tubing internal wall opposing each sensor and from which the round trip transit time of the signals is measured and the sound velocity calculated from the two measured round trip transit times and the differential between the known transverse lengths. Flexible tubing is placed in the slot of a measuring head which deforms it to provide the two points at one location or the slot has two sections of different transverse length along its length with a point at each section.

15 Claims, 4 Drawing Sheets

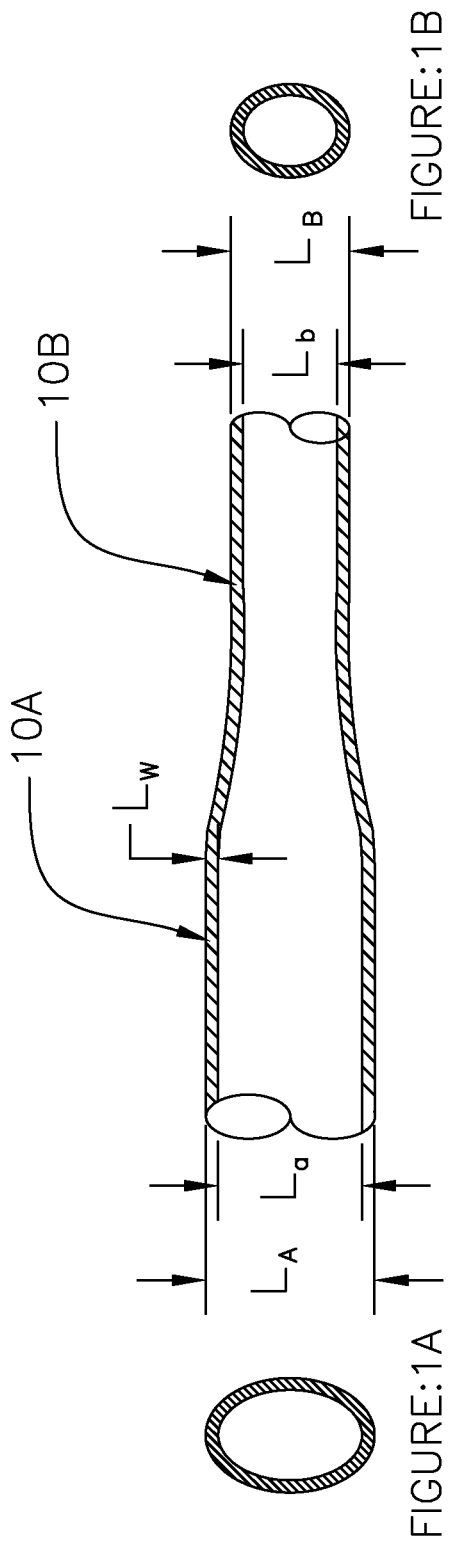

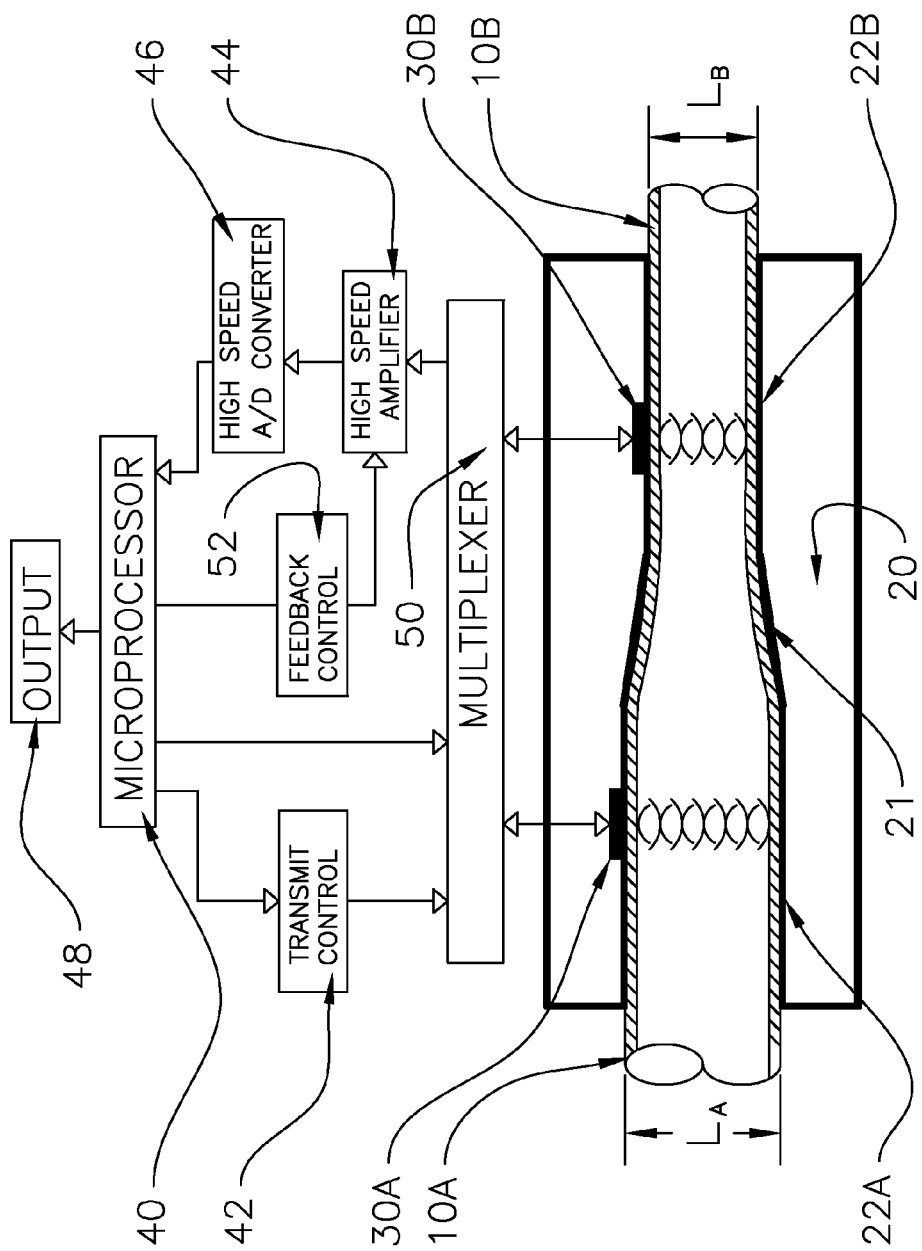
FIGURE: 2

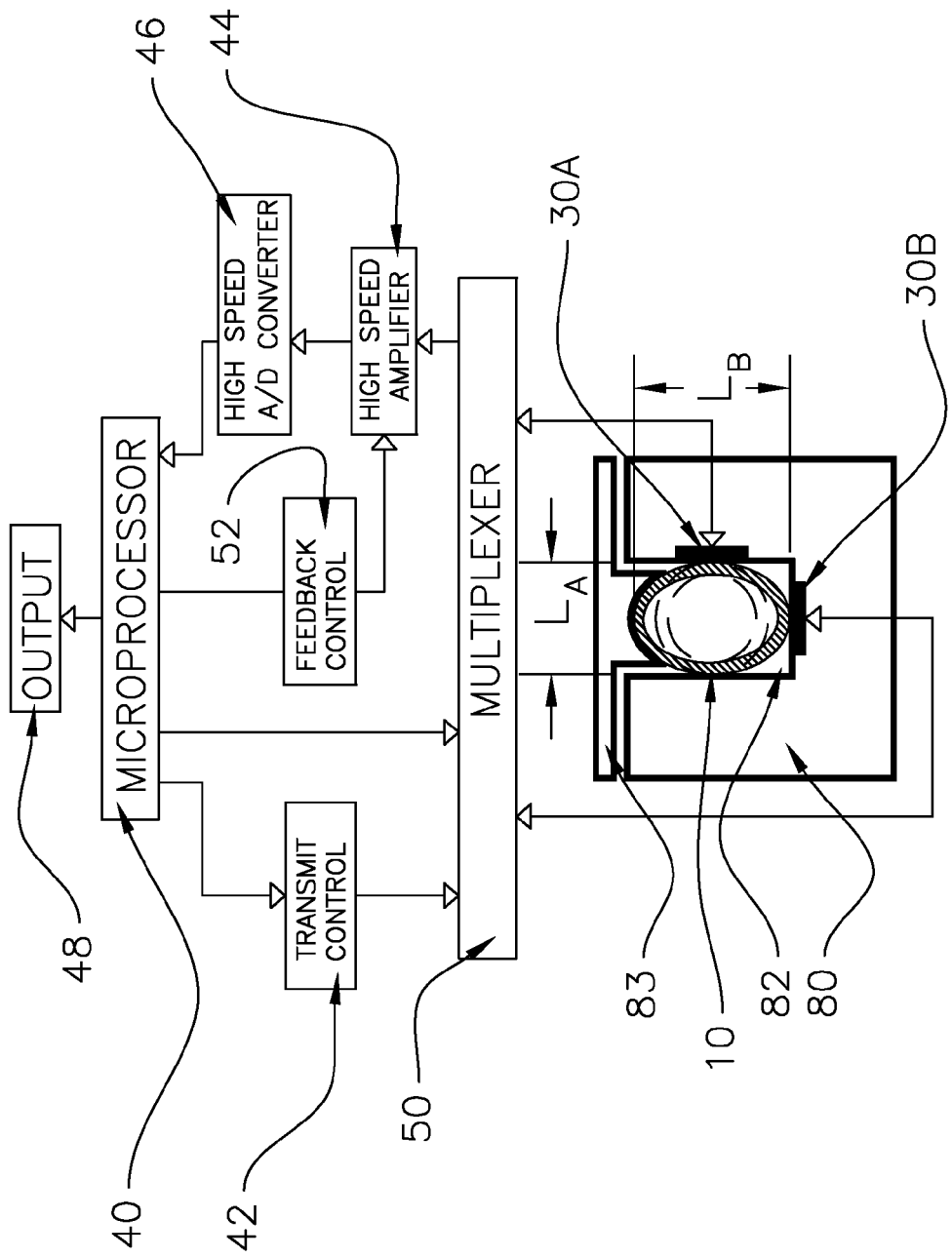
FIGURE: 3

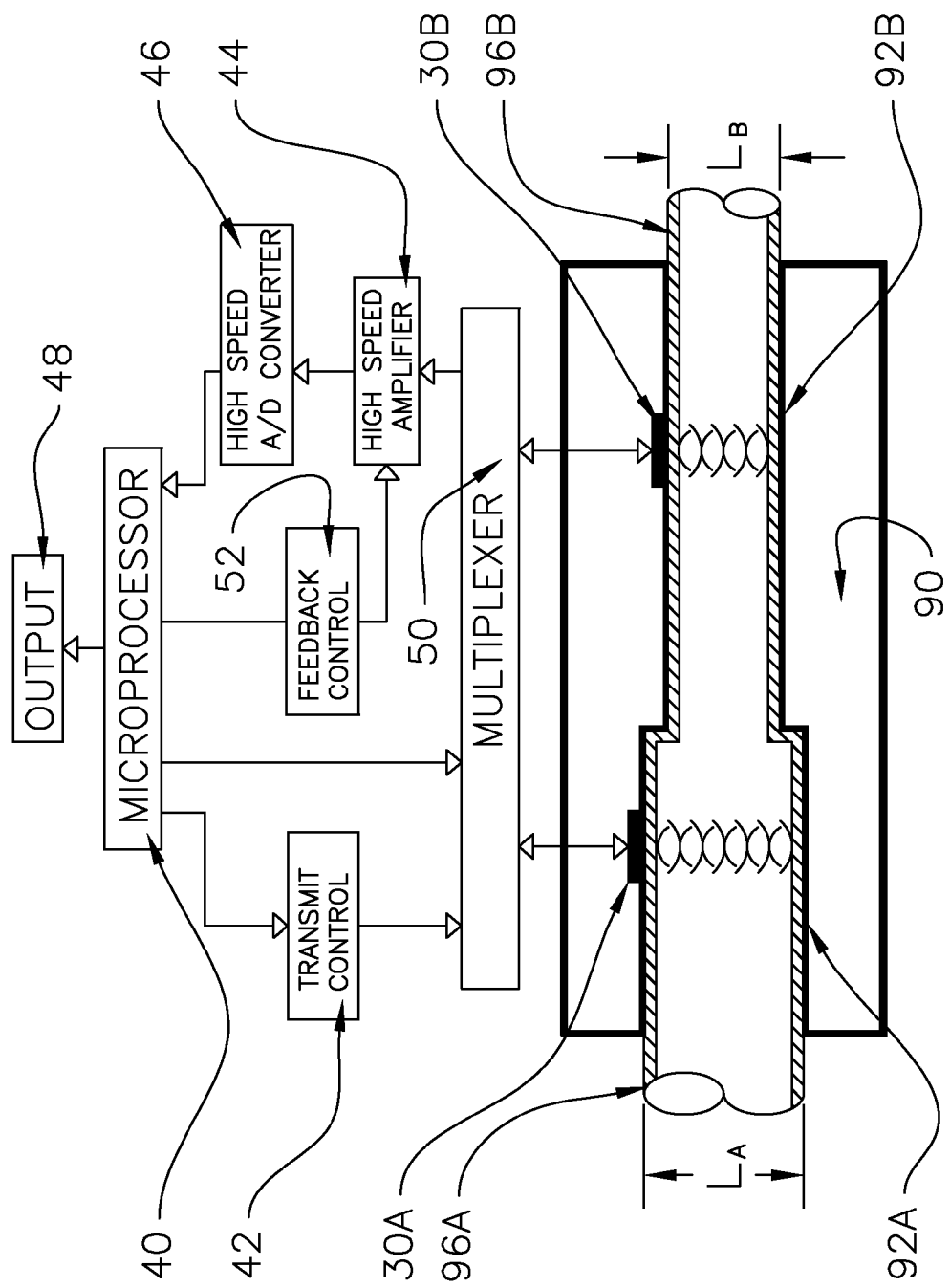
FIGURE: 4

APPARATUS AND METHOD FOR NON INVASIVE MEASUREMENT OF PROPERTIES OF A FLUID FLOWING IN A FLEXIBLE TUBING OR CONDUIT

FIELD OF THE INVENTION

The present invention relates to an apparatus and method for non-invasively measuring the sound velocity of a fluid flowing in flexible or rigid tubing.

BACKGROUND OF THE INVENTION

The term "sound velocity" is a recognized shorthand expression describing a characteristic of the speed at which sound waves travel in a medium. The speed of sound varies depending on the medium through which the sound waves pass. It usually is a parameter used in describing properties of different substances or mediums. Knowing the value of the sound velocity of a particular medium, such as a flowing fluid, liquid or gas, permits many different characteristics or properties of the fluid to be determined. Using the sound velocity together with appropriate mathematical relationships allows for determination of various characteristics or properties of the medium such as its density, purity concentration, components of the medium composition, etc.

Several different types of apparatus exist for measuring the velocity of a signal, hereafter referred to as the "sound velocity", in a fluid flowing in flexible or rigid conduit type tubing. The term "tubing" is used hereafter to define both the flexible and rigid type except as otherwise expressly disclosed. The different apparatus types for measuring sound velocity generally are of either the contact or the non-invasive type. In the contact type, some part or parts of the measuring apparatus come into direct contact with the fluid. In the non-invasive type, the sound velocity is measured without any part of the measuring apparatus coming into contact with the fluid.

In many applications it is preferred that the sound velocity measurement be made non-invasively. The non-invasive measurement has advantages in medical and biotechnology applications, as well as in handling hazardous chemicals and ultra pure liquids such as are used in semiconductor processing systems. The advantages primarily result from the fact that no part of the measuring apparatus comes in contact with the fluid that might lead to contamination while making the measurements needed to determine the sound velocity. Also, when dealing with hazardous and corrosive fluids possible damage to parts of the measuring apparatus is avoided since there is no contact with the fluid.

Several instruments are known for making the sound velocity measurement non-invasively. For example, in U.S. pre-grant patent publication 2006/0052963 two pairs of ultrasonic transducers, or sensors, are used. One of the sensors of each pair is a transmitter of ultrasonic (electro-mechanical) signal energy and the other is a receiver. The transmitting and receiving sensors of each pair are mounted on opposite sides of the tubing in which the fluid is flowing. The transit time of a signal from the transmitting sensor of each pair along a respective path through the fluid and the two tubing walls to the receiving sensor of the pair is measured. The sound velocity of the signal in the liquid is calculated from the results of the two one-way transit time measurements. While such apparatus is effective in determining the sound velocity, it requires four sensors. Also, in some of the disclosed embodiments a special mounting is required for the sensors of the two pairs so that the transmitter and receiver sensors are offset at an angle from the tubing wall and from each other along the tubing length. Here the ultrasonic signal is transmitted by one sensor of each pair upstream and downstream of the fluid flow to the other sensor of the pair on the tubing opposite side.

In U.S. Pat. No. 7,481,114 a flexible tubing is mounted in a fixture having a device that produces a force to deform the tubing external and internal dimensions at one point in a direction transverse to the tubing length. The tubing cross-sectional dimensions are hereafter referred to as "transverse length" since they are in a direction that is perpendicular to the tubing longitudinal axis and the fluid flowing in it. The force producing device deforms the normally circular flexible tubing cross section by a first amount to form a first path, or transverse length. The first path has a first acoustic path length along which a signal is transmitted by an ultrasonic sensor and reflected back to the sensor after reflection from the opposing internal wall of the deformed tubing. The round trip signal transit time along the first path is measured. The force producing device is operated again to further deform the tubing transverse length dimension to form a second path which is co-linear with the first path but that has an acoustic path length different from that of the first path. A signal is transmitted by the sensor and reflected back to it along the second co-linear path. The round trip transit time of the signal along the second path is measured. The sound velocity is then calculated based on the two measured round trip transit times. In this system the separate force producing device must be provided and some apparatus also must be provided for operating this device at the proper times in relation to the transmission and reception of the signals over the two paths. This effectively prevents sound velocity from being measured on a substantially continuous basis. Also, the apparatus cannot work with rigid tubing.

Accordingly, it is desired to provide a more simplified apparatus and method for accomplishing non-invasive measurement of the sound velocity of a flowing fluid which can be done on a continuous basis.

BRIEF DESCRIPTION OF THE INVENTION

In accordance with the invention, an apparatus is provided to non-invasively measure sound velocity in a fluid flowing in either elastic or rigid tubing. Elastic tubing is made of an elastomeric material that can be deformed or squeezed to change its cross-sectional, or transverse, length. In the invention, a single sensor is mounted at two different points of the tubing that have different transverse lengths. A pulse echo technique is used to measure the round-trip transit time of a signal that is transmitted by the sensor at each of the two tubing points along an acoustic path through a wall of the tubing and reflected back to the sensor from the tubing opposing internal wall. The round trip transit time of the signal for each of the two paths is measured. The transit times are different because of the different transverse lengths of the tubing and the acoustic paths at each of the two points where the measurements take place. By knowing the differential between the transverse lengths of the tubing at the two points and the results of the two round-trip transit time measurements the sound velocity of the fluid flowing in the tubing can be calculated. The sound velocity calculation is independent of the tubing wall thickness.

In one embodiment of the invention for use with elastic tubing, the tubing is held in the elongated slot of a measuring head in which the slot has two sections of different known transverse lengths (distances across the slot). When placed in the slot, the elastic tubing is deformed, or squeezed, into a somewhat elliptical shape and the tubing is firmly held in the slot. One sensor is placed in the measuring head adjacent to the tubing at a point of each slot section. Each sensor both transmits signal energy though the wall of the tubing to be reflected from the opposing inner wall back to the sensor. The measured value of the round-trip transit time of the signal energy transmitted along a path to and reflected from the tubing internal wall at each point will be different because of the different outer transverse lengths of the deformed tubing at the two points along the tubing length. The differential of the transverse lengths at the points of the two sections is known from the construction of the slot or from measurement and the sound velocity is calculated from this and the measured values of the two round trip transit times.

In another embodiment of the invention for use with elastic tubing, there is a measuring head with a slot having one location along its length in which the elastic tubing is placed where it is deformed from its normal circular shape to a more generally elliptical shape. Two sensors are mounted at different points of the single location at an angle, preferably substantially orthogonal, to each other around the tubing. Here, the measured round-trip transit time of the signal from each sensor reflected from the opposing internal tubing wall is different because of the different transverse lengths of the deformed, or squeezed, tubing at the single location. Here also, the sound velocity is calculated using the two measured round-trip transit times and the known differential of the two transverse lengths.

In an embodiment of the invention for measuring the sound velocity of a fluid flowing in rigid tubing, the tubing itself is formed with two, preferably adjacent, sections of different transverse length. The rigid tubing is placed in the slot of a measuring head in which a sensor is mounted at a point of the slot for each tubing section. The round-trip transit time of signals transmitted from each sensor and reflected back to it from the opposing internal wall of the rigid tubing along a respective path is measured. As in the other embodiments, the signal sound velocity is calculated from the two measured round-trip transit times and the known differential of the transverse lengths of the rigid tubing at the two points where the sensors are mounted. Is this embodiment, instead of using a measuring head with a slot, the two sensors can be mounted directly to the wall of the rigid tubing at the two points.

Each embodiment of the invention includes a microprocessor that controls the times of transmission and reception of the signals by the sensors. The microprocessor is pre-programmed with the known differential value of the transverse lengths at the two points where the sensors are located. The microprocessor also performs the measurements of the two round trip transit times and the calculation of the sound velocity.

In all of embodiments of the invention, only two sensors are required. The transit time measurement for both sensors preferably is made at substantially the same time to minimize the effects of temperature change of the flowing fluid. In all of the embodiments of the invention, the calculation of the sound velocity is independent of tubing wall thickness and change in tubing wall thickness due to temperature changes and tubing material. By eliminating the effect of these external parameters, a more accurate measurement of the sound velocity can be obtained. In all of the embodiments of the invention, the signals are transmitted from and reflected back to each sensor substantially transverse to the tubing longitudinal axis and the fluid flow.

BRIEF DESCRIPTION OF THE DRAWINGS

Other objects and advantages of the present invention will become more apparent upon reference to the following specification and annexed drawings in which:

FIG. 1 is a plan view of a piece of tubing having two sections of different transverse (cross-sectional) length;

FIGS. 1A and 1B are end views of the tubing piece of FIG. 1;

FIG. 2 is a top plan view of an embodiment using a pulse echo technique for measuring the round-trip transit time of signal energy through the tubing at two different points spaced along the length of the slot of a measuring head;

FIG. 3 is an end view in cross-section of a measuring head of an embodiment of the invention in which the two round-trip transit time measurements are made at a single location along the tubing length; and FIG. 4 is a top view of an embodiment of the measuring head of the invention for making the sound velocity measurement in rigid tubing.

DETAILED DESCRIPTION OF THE INVENTION

Referring to FIG. 1, a piece of tubing 10 in which a fluid is flowing is illustratively shown having two sections 10A and 10B of different transverse length. The tubing can be of any material compatible with the fluid to be flowing in it and can transmit ultrasonic (electro-mechanical) energy through its wall. The tubing can be of metal or rigid, semi-rigid or deformable plastic. Suitable types of elastomeric deformable plastic are, for example, silicon, Teflon, PVC.

The tubing 10 can have a normal circular cross-section along its length or it can be of other shapes, such as rectangular or square. It is assumed for purposes of explanation, that the tubing 10 of FIG. 1 is part of a longer piece (not shown) of an original shape that has been deformed, or "squeezed", to be somewhat elliptical along the lengths of the two sections 10A and 10B, as shown by the end views of FIGS. 1A and 1B. The deformation or squeezing takes place for example when elastic tubing 10 is placed in a slot of a measuring head in which the slot transverse length is less than the normal circular, or square or rectangular, elastic tubing outer diameter. Rigid or semi-rigid tubing is pre-formed or supplied with the desired shaped sections 10A and 10B along its length.

The tubing first section 10A is shown as having an outer transverse length LA and an inner transverse length La. The first section, 10A can be the normal shape of the tubing. The second tubing section 10B, has smaller outer and inner transverse lengths LB and Lb produced by deformation of elastic tubing or pre-forming a rigid tubing. In each section 10A and 10B the tubing wall thickness is Lw is the same and does not change. The foregoing dimensions hereafter apply to all embodiments of the invention.

FIG. 2 is an embodiment of the invention for use with deformable tubing. There is a pre-molded or machined measuring head 20 which can be of any suitable material, such as plastic. The head 20 has a continuous slot 22 along its length formed by a bottom wall and two spaced opposing side walls. The slot has a first section 22A having a known transverse length (distance across the slot between the side walls) that tapers down in a transition section 21 to a second slot section 22B having a known smaller transverse length than that of section 22A. When a piece of elastic deformable tubing 10 of greater outer diameter than that of the slot transverse length is placed in the slot 22 it will be deformed, or squeezed, to have the outer transverse lengths LA and LB (transverse length perpendicular to the two opposing slot walls) that are those of the slot of sections 22A and 22B. The transverse lengths of the slot sections 22A and 22B correspond to the transverse lengths LA and LB of the two tubing sections 10A and 10B of FIG. 1. The transverse length of the slot section 22A only has to be slightly smaller than the normal transverse lines of the deformable tubing. The slot sections transverse lengths LA and LB are known from manufacturing specifications of the measuring head 20 or from direct measuring. Since LA and LB are known and fixed, the differential value LA−LB also is known and does not change.

A respective ultrasonic transmit/receive transducer, or sensor, 30A and 30B is mounted in the head 20 in a side wall of each of the slot sections 22A and 22B. While the sensors 30A and 30B are shown on the same slot wall, they can be on the opposite walls of the slot. Each sensor 30 has a face that is close to the face of the slot wall. Since the tubing in the slot is squeezed, it effectively bonds to the face of the measuring head wall whose material serves as a coupling medium to convey ultrasonic energy to and from each sensor and the tubing held between the slot walls. The sensors 30 can be of any suitable piezoelectric material such as PZT (lead zirconate titanate) or PVDF (PolyVinyliDene Fluoride).

The face of each sensor 30 is generally parallel to the outer and inner walls of the tubing in the two slot sections and is generally transverse (perpendicular) to the tubing longitudinal axis and the fluid flowing in the tubing. Each sensor 30 has a respective acoustic path length APL for the signal that is transmitted by it and received after reflection from the tubing internal opposing wall. Thus, APL for 30A=2(La+Lw)

APL for 30B=2(Lb+Lw)

A programmable microprocessor 40 of conventional construction, preferably with an internal memory, is suitably programmed to perform the functions to be described. The microprocessor is pre-programmed with the known transverse length differential value LA−LB. The microprocessor has an output 48 which can be of any conventional type, such as a digital readout, video display, or any other suitable apparatus for displaying the results of its measurements and calculations.

The microprocessor 40 controls a transmit control circuit 42 which provides electrical signals, preferably in bursts, to each of the sensors 30A and 30B. The transmit control circuit 42 includes either a suitable source of the signals that runs continuously and whose output is gated to the sensors 30 to provide the signal bursts or a generator that the microprocessor activates for the times of the bursts. The microprocessor 40 also operates a multiplexer 50 that controls transmission and reception of the signals by the sensors 30A and 30B. The electrical signals provided to each sensor 30 by the transmit control circuit 42 are converted into electro-mechanical energy that is transmitted by the sensor. This energy passes through the tubing outer wall and the flowing fluid and is reflected from the tubing internal wall opposing the sensor back through the flowing fluid and the tubing outer wall to the same sensor. This is sometimes called the pulse echo technique. The sensor 30 then converts the received reflected electro-mechanical energy back to an electrical signal.

Microprocessor 40 also operates to control reception of the reflected energy. That is, there is a pause between the transmission of each burst of signals by a sensor to allow for reception of the reflected energy and the calculation of the round-trip transit time before the next signal burst is transmitted. A high speed amplifier 44 receives the signal from each sensor 30A and 30B of the energy reflected from the internal wall of each tubing section 22A and 22B. A feedback control circuit 52 is provided to normalize the amplitude of the received signals to a substantially fixed value and these signals are applied to a high speed analog/digital (A/D) converter 46 to be converted to digital form. The digital signals are applied to the microprocessor 40 for use in various computational functions.

The time of transmission of the energy by each sensor 30 is known at the microprocessor 40 since it controls this time. The microprocessor also knows the time of reception of the reflected signals as supplied by the A/D converter 46. Therefore, the microprocessor can calculate the round trip transit time of the signals transmitted from each sensor 30 and received back to it after reflection from the tubing opposing inner wall. Alternate methods of calculating the round-trip transit time can be used such as starting a clock running at the time of the signal transmission and stopping the clock at the time of the reflected signal reception.

The circuit preferably operates so that the two round-trip transit times of the signals in the tubing sections 22A and 22B are measured sequentially or at substantially the same time. In a preferred embodiment of the invention, the two transit times are measured as close to simultaneously as possible so that any change in the temperature of the fluid flowing in the tubing 10 between the two slot sections 22A and 22B will not adversely affect the accuracy of the measurements and the final calculation of the sound velocity. If desired, the measuring head can be provided with a non-invasive sensor for measuring the temperature, such as described in U.S. Pat. No. 7,661,294 granted to the inventor of this invention, to improve the accuracy of the measurements.

The calculation of the sound velocity is explained as follows.

The tubing outer transverse lengths LA and LB can be written as $$LA = 2Lw + La \tag{1}$$

and $$LB = 2Lw + Lb \tag{2}$$

where:

LA and LB are the outer transverse lengths of the two tubing sections.

Lw=wall thickness of a given tubing. This is the same for both tubing sections and does not change at the location of the tubing deformation from the tubing normal overall shape.

La=tubing inner transverse length at slot section 22A at which sensor 30A is located.

Lb=tubing inner transverse length at sensor 30B location in slot section 22B.

From equations (1) and (2):

$$LA - LB = La - Lb, \text{ hereafter called } LAB \tag{3}$$

where

LAB=fixed differential of the tubing outer transverse lengths at the locations of sensors 30A and 30B. LAB is known from the cross-sectional lengths of the slot in each of the sections 22A and 22B which sets each of LA and LB. The value of LAB is programmed into the microprocessor.

Using the pulse echo technique with a single sensor 30 at a point of each slot section 22A and 22B, the respective round trip travel time ta and tb of the energy at each sensor location of the slot sections 22A and 22B is determined as follows:

$$ta = \frac{2tw + 2La}{V} \tag{4}$$

$$tb = \frac{2tw + 2Lb}{V} \tag{5}$$

-continued $$ta - tb = \frac{2(La - Lb)}{V} \qquad (6)$$

where V is the sound velocity of the flowing fluid.
Since from equation (3), La−Lb=LA−LB=LAB, therefore:

$$V = \frac{2LAB}{ta - tb} \qquad (7)$$

where ta−tb is the differential of the two round trip measurements.
Let: ta−tb=tab so that $$V = \frac{2LAB}{tab} \qquad (8)$$

Thus, by knowing the fixed differential LAB of the transverse lengths at the points of each of the sensors 30A and 30B, as set by the transverse lengths of the measuring head slot sections 22A and 22B, and measuring the two round trip times ta and tb, from which the differential elapsed time tab is calculated, the sound velocity V of the flowing fluid is calculated by the microprocessor using equation (8).

It is noted that the sound velocity of the tubing wall Lw is different from that of the flowing liquid. However, as shown above in equation (8), the sound velocity measurement is independent of the tubing wall thickness Lw. As also can be seen from equation (8), the accuracy of the measurement can be increased by increasing the differential LAB of the transverse lengths of the two sections because tab remains the same.

Typical parameters for the instrument of the invention, by way of example, are:
a. material of tubing (deformable or rigid)—PVC, Teflon, any plastic materials.
b. outside diameter of tubing before squeeze—⅛" minimum to 1" maximum.
c. wall thickness of tubing 0.01" to 0.1"maximum
d. tubing inner and outer transverse lengths after squeeze—, approximately 20% to 30% less than before, the squeeze. The tubing wall thickness Lw is not changed by the squeeze.
e. distance between the two sensors 30A and 30B—minimum 0.5", maximum 2.0".
f. transverse length LA and LB across the slot at the two sections 22A and 22B—different for each tubing and accuracy desired.
g. length of slot sections 22A and 22B—0.25" to 1.00"
h. operating frequency—2 MHZ minimum-20 MHZ maximum, depends on resolution of system that is desired.
i. duration of pulse bursts of the ultrasonic energy. Minimum 100 nano seconds, Maximum 1 microsecond.
j. time between the bursts—10 microseconds minimum to 5 milliseconds maximum.
Other frequencies, burst durations and burst timing as well as other physical dimensions can be used depending on the material and size of the tubing, the type of fluid and the accuracy of the result needed.

FIG. 3 shows a further embodiment of the invention in which both of the sensors are positioned at a single location along the tubing length. The same reference numerals are used for the same components of the embodiment of FIG. 2.

Here, there is a measuring head 80 that has a slot 82 in which the tubing is placed. The slot 82 has a transverse dimension LA across its width so that when the tubing is placed in the slot it will have the same outer transverse length dimension LA that corresponds to the first tubing section 10A of FIGS. 1 and 2. There is a cover 83 at the top of the slot 82 whose inner surface together with the bottom wall of the slot sets the transverse length dimension LB. The cover 83 can be hinged to the measuring head, have a snap fit, slide over the slot location, or any other suitable type of fastening configuration. The tubing 10 in the slot 82 has an original dimension such that when deformed in the slot it will engage the inner wall of the cover 83. The tubing therefore will assume a second transverse length LB that is orthogonal to the first length LA and corresponds to the second tubing section 10B of FIGS. 1 and 2. The tubing will have its normal circular shape in locations outside of the slot 82. Therefore, the transverse length differential LA−LB (LAB) is known and fixed.

The two transmit/receive sensors 30A and 30B are mounted in the measuring head 80 at an angle to each other at two different points at one location along the slot length to address respective tubing first and second transverse lengths LA and LB. As shown in FIG. 3, sensor 30A is at a side wall of the slot and sensor 30B at the bottom wall, making the sensors orthogonal to each other. The faces of the two sensors 30A and 30B are parallel to the axis of the fluid flowing in the tubing and to the to me outer wall and transmit energy generally transverse to each.

The circuit of the embodiment of FIG. 3 operates similarly to that of FIG. 2 in that the two sensors 30A and 30B are supplied with signals from the transmit control circuit 42. The round-trip transit time of the signals transmitted by each sensor and received after reflection from the tubing opposing inner wall is measured in the manner described above. The sound velocity of the signal is also calculated in the same manner as described above.

FIG. 4 shows another embodiment of the invention that is useful with semi-rigid or rigid tubing, that is, tubing that cannot be readily deformed such as by placing it in a slot. Here there is a tubing 96 of a rigid or semi-rigid material such as hard or soft PVC that is configured with two sections 96A and 96B of different outer and inner diameters and the same wall thickness in each section. There can be a transition section between the two sections if needed or desired, such as shown in FIG. 2. The two tubing sections can be molded in the desired shape or be joined by any suitable coupling or transition member (not shown) that couples the two tubing sections of different diameters together. If the tubing is of metal, the ends of tubing sections of different diameter can be welded or soldered together. The tubing sections 96A and 96B can be of any shape with circular shape being preferred. The outer diameters of the tubing sections 96A and 96B correspond to the transverse lengths LA and LB of tubing 10 of FIGS. 1-3 and the inner diameters correspond to the transverse lengths La and Lb of FIGS. 1-3.

A measuring head 90 is used that has a slot 92 with sections 92A and 92B each of a transverse width that corresponds to the respective outer diameters of the two tubing sections 96A and 96B. The transverse and elongated lengths of the slot sections are selected as fits the application of needed accuracy and material and dimensions of the tubing sections. There is a sensor 30A and 30B in the head 90 at the wall of each of the slot sections 92A and 92B. In this embodiment of the invention, the rigid tubing 96 is placed in slot 92 so that the respective sensors 30A and 30B are opposite and contact the corresponding wall of the tubing sections 96A and 96B. There is no deformation of the tubing 96 as it is placed in the slot 92. If desired, a coupling material such as petroleum jelly can be used between the sensors and the tubing outer wall. Also if desired, the two sensors can be mounted directly to the wall of the tubing thereby eliminating the need for the head 90.

The operation of the apparatus of FIG. 4 is the same as that previously described in that the round-trip transit time of the signals from each of the sensors 30A and 30B in the first and second acoustic paths of the tubing sections 92A and 92B will each be measured by the microprocessor 40. From these measurements and the known differential of the tubing sections transverse lengths pre-programmed into the microprocessor 40, the sound velocity of the flowing fluid will be calculated as described above.

The invention has a number of advantages. The microprocessor 40 can be programmed to calculate and provide any property or characteristic of the fluid that can be determined using the sound velocity information that has been calculated. Thus, the invention can provide on-line real time measurement of liquid properties and characteristics using sound velocity information.

The disposable elastic tubing of various types of existing equipment can be utilized without modification. Also, there is no need to design special fixtures or cups of specific acoustic length since the calculation of the sound velocity is independent of fluid flow rate change, and tubing wall thickness. In many situations it is also relatively independent of temperature change. The invention is useful in industrial applications such as where corrosive liquids, e.g. $H_2SO_4$, $HNO_3$ can be monitored continuously.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. Apparatus for noninvasive measurement of the sound velocity of a fluid flowing in a tubing, comprising:
    a measuring head having an open slot with flat planar walls in which the tubing is placed, said slot having three orthogonal wall portions arranged such that both ends of a bottom wall section are contacted by one end of each of two opposing side wall sections, which wall portions contact the tubing, said slot having first and second points of different transverse length positioned at, at least one location of the slot longitudinal length, each slot transverse length at said first and second points forming a respective acoustic path of a different length;
    a source of energy signals;
    a respective first and second transmit/receive sensor mounted in said measuring head adjacent said slot first and second points of different transverse length, each said sensor transmitting signals from said energy source along a respective path through a wall of the tubing and the fluid flowing therein and receiving the signals reflected from the tubing internal wall back to a said sensor; and
    a circuit for measuring for each said first and second sensor the round-trip transit time of the signals from the time of transmission to the time of reception after reflection from the tubing internal wall, and for calculating the sound velocity of the flowing fluid from the round-trip transit times measured for the signals of the first and second sensors.

2. The apparatus as claimed in claim 1 wherein said circuit calculates the sound velocity also based on the differential of the transverse lengths at said first and second points of said slot.

3. The apparatus as claimed in claim 2 wherein the different transverse lengths are determined by the lengths between opposing walls of the slot and are known by said circuit before the calculation of sound velocity takes place.

4. The apparatus as claimed in claim 2 wherein said slot is to hold an elastic tubing and has dimensions such as to deform the tubing to produce the different transverse lengths forming the different paths for said first and second sensors.

5. The apparatus as claimed in claim 4 wherein said slot provides the first and second points at one location along the length of the tubing, and said first and second sensors are mounted in said measuring head at different walls of said slot that are generally orthogonal to each other.

6. The apparatus as claimed in claim 4 wherein:
    said slot is elongated and has first and second sections in which the opposing side walls are at different distances from each other so there are different transverse lengths across the slot of the respective first and second section in which the tubing is to be placed to have a respective different transverse length across a tubing in each slot section; and
    wherein said first and second sensors are mounted in said head at a respective point in a wall of a said slot first and second section.

7. The apparatus as claimed in claim 2 wherein said slot is elongated and has first and second sections of different transverse length across the respective section in which a rigid tubing having first and second sections of different transverse length is to be placed; and
    wherein said first and second sensors are mounted in said head at a respective point of said first and second slot section.

8. The apparatus as claimed in claim 2 wherein said circuit operates to calculate the sound velocity V using the formula $$V = \frac{2LAB}{tab}$$

where:
    LAB=the differential of the transverse lengths at the two points, and
    tab=the differential of the two round trip time measurements.

9. The apparatus as claimed in claim 1 wherein said circuit comprises a microprocessor for controlling the times of transmission of the signals, measuring the round trip transit times and calculating the sound velocity.

10. The apparatus as claimed in claim 9 further comprising a multiplexer controlled by said microprocessor to control the times of transmission and reception of signals by said first and second sensors.

11. The apparatus as claimed in claim 9 wherein said microprocessor operates to calculate the sound velocity V using the formula $$V = \frac{2LAB}{tab}$$

where:

LAB=the differential of the transverse lengths at the two points, and tab=the differential of the two round trip time measurements.

12. The apparatus as claimed in claim 1 wherein each said first and second sensor is positioned to transmit the energy perpendicular to the tubing longitudinal axis and the fluid flow.

13. A method of determining the sound velocity of a fluid flowing in a tubing comprising the steps of:
- providing an elastically deformable tubing in a head having an open slot with three orthogonal planar walls arranged so that the ends of a bottom wall are contacted by an end of each of two opposing side walls, at least one of said walls having a step therein so that the slot has first and second points of different transverse length, said tubing contacting and being shaped by the walls so as to have two points of different transverse lengths along the tubing length, each transverse length forming an acoustic path;
- providing a transmit/receive sensor external of the tubing at each of the two points of different transverse length;
- transmitting a signal from each of said sensors through a wall of the tubing and the fluid blood flowing therein and receiving the signal reflected from the internal wall of the tubing opposing the respective sensor;
- measuring for each sensor the round-trip transit time of the signal from the time of transmission to the time of reception after reflection from the tubing opposing internal wall; and
- calculating the sound velocity of the flowing fluid from the round-trip transit times measured for the signal of each sensor.

14. The method as claimed in claim 13 wherein the step of providing the tubing and head with a slot having two points of different outer transverse widths comprises:
- squeezing said tubing at a single location along its length; and wherein the step of providing the sensors comprises:
- placing a first sensor at an angle to a second sensor at one location.

15. The method as claimed in claim 13 wherein said step of calculating comprises:
- calculating the sound velocity V using the formula $$V = \frac{2LAB}{tab}$$

where:

LAB=the differential of the transverse lengths at the two points, and tab=the differential of the two round trip time measurements.

* * * * *